(12) United States Patent
Lippa et al.

(10) Patent No.: US 7,276,602 B2
(45) Date of Patent: Oct. 2, 2007

(54) ISOTHIAZOLE DERIVATIVES USEFUL AS ANTICANCER AGENTS

(75) Inventors: Blaise Lippa, Mystic, CT (US); Tricia Ann Kwan, Groton, CT (US); Joel Morris, East Lyme, CT (US); Susan D. LaGreca, Old Lyme, CT (US); Matthew David Wessel, Ledyard, CT (US)

(73) Assignee: Pfizer Inc, New York, NY (US)

( * ) Notice: Subject to any disclaimer, the term of this patent is extended or adjusted under 35 U.S.C. 154(b) by 77 days.

(21) Appl. No.: 10/626,406

(22) Filed: Jul. 24, 2003

(65) Prior Publication Data

US 2004/0152691 A1    Aug. 5, 2004

Related U.S. Application Data

(60) Provisional application No. 60/398,386, filed on Jul. 25, 2002.

(51) Int. Cl.
*C07D 412/02* (2006.01)
*C07D 417/12* (2006.01)

(52) U.S. Cl. .................. 544/238; 544/405; 546/271.1; 548/213

(58) Field of Classification Search ................ 544/328, 544/405; 546/271.1; 548/213
See application file for complete search history.

(56) References Cited

U.S. PATENT DOCUMENTS 5,409,930 A    4/1995  Spada et al.
5,952,359 A    9/1999  Godfrey et al.
6,235,764 B1 * 5/2001  Larson et al. ............... 514/372
6,380,214 B1    4/2002  Gant et al.
6,569,878 B1    5/2003  Chong et al.

OTHER PUBLICATIONS

Edsjo, Anders, et al., Differences n Early and Late Responses between Neurotrophin-stimulated trkA- trkC-transafected SH-5Y5Y Neuroblastoma Cells, Cell Growth & Differentiation, vol. 12, pp. 39-50 (Jan. 2001).*

* cited by examiner

*Primary Examiner*—Kamal A. Saeed
*Assistant Examiner*—Andrew B. Freistein
(74) *Attorney, Agent, or Firm*—Steve Zelson; David L. Kershner

(57) ABSTRACT

The invention relates to compounds of the formula 1

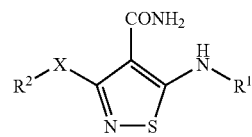

or pharmaceutically acceptable salts, prodrugs, solvates or hydrates thereof, wherein wherein X, $R^1$, and $R^2$ are as defined herein. The invention also relates to pharmaceutical compositions containing the compounds of formula 1 and to methods of treating hyperproliferative disorders in a mammal by administering the compounds of formula 1.

18 Claims, No Drawings

ISOTHIAZOLE DERIVATIVES USEFUL AS ANTICANCER AGENTS

This application claims benefit of U.S. Provisional Application No. 60/398,386, filed Jul. 25, 2002.

BACKGROUND OF THE INVENTION

This invention relates to novel isothiazole derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype. It has been shown that certain tyrosine kinases may be mutated or overexpressed in many human cancers such as brain, melanoma, lung, squamous cell, bladder, gastric, breast, head and neck, oesophageal, gynecological and thyroid cancers. Furthermore, the overexpression of a ligand for a tyrosine kinase receptor may result in an increase in the activation state of the receptor, resulting in proliferation of the tumor cells or endothelial cells. Thus, it is believed that inhibitors of receptor tyrosine kinases, such as the compounds of the present invention, are useful as selective inhibitors of the growth of mammalian cancer cells.

It is known that growth factors such as the neurotrophin family activate receptor tyrosine kinases such as trks. The neurotrophin family of growth factors includes nerve growth factor (NGF), brain derived neurotrophic factor (BDNF), neurotrophin-3 (NT-3) and neurotrophin 4/5 (NT-4/5). These basic proteins are approximately 120 amino acids in length, share approximately 50% sequence homology, and are highly conserved among mammalian species (Issackson et al., FEBS Lett. 285:260–64, 1991). NGF was the first growth factor discovered and remains the best characterized neurotrophin. NGF is required for normal development of sensory and sympathetic neurons and for normal function of these cells in adult life (Levi-Montalcini, Annu. Rev. Neurosci. 5:341–362, 1982; Yankner et al., Annu. Rev. Biochem 51:845–868, 1982).

Neurotrophin binding and activation of a set of high affinity receptors (trks) is necessary and sufficient to mediate most of the biological effects of the neurotrophins. The trks are transmembrane proteins that contain an extracellular ligand binding domain, a transmembrane sequence, and a cytoplasmic tyrosine kinase domain. The trks comprise a family of structurally related proteins with preferential binding specificities for the individual neurotrophins. TrkA, which is sometimes referred to as trk, is a high-affinity receptor for NGF, but it can also mediate biological responses to NT-3 under particular conditions (Kaplan et al. Science 252:554–558, 1991; Klein et al., Cell 65, 189–197, 1991; Cordon-Cardo et al., Cell 66:173–183, 1991). TrkB binds and mediates functions of BDNF, NT-3, and NT4/5 (Klein et al. Cell 66:395–403, 1991; Squinto et al., Cell 65:885–893, 1991; Klein et al. Neuron 8:947–956, 1992). TrkC is relatively specific for NT-3 (Lamballe et al., Cell 66:967–979, 1991).

The Trk family of receptor tyrosine kinases is frequently expressed in lung, breast, pancreatic and prostate cancers. See, Endocrinol. 141: 118, 2000; Cancer Res., 59: 2395, 1999; Clin. Cancer Res. 5: 2205, 1999; and Oncogene 19: 3032, 2000. The tyrosine kinase activity of Trk is believed to promote the unregulated activation of cell proliferation machinery. Recent pre-clinical data suggests that Trk inhibitors suppress the growth of breast, pancreatic and prostate tumor xenografts. Furthermore, it is believed that Trk inhibition may be tolerated in cancer patients. It is also believed by those in the art that inhibitors of either TrkA or TrkB kinases have utility against some of the most common cancers, such as brain, melanoma, squamous cell, bladder, gastric, pancreatic, breast, head, neck, oesophageal, prostate, colorectal, lung, renal, kidney, ovarian, gynecological, and thyroid cancer. It is further believed that additional therapeutic uses of Trk inhibitors include pain, neuropathy and obesity.

Isothiazole derivatives are known and have identified as herbicides in U.S. Pat. Nos. 4,059,433 and 4,057,416, both assigned to FMC Corporation. Isothiazoles derivatives useful for prolferative disease are referred to in U.S. Pat. No. 6,235,764, assigned to Pfizer, Inc.

SUMMARY OF THE INVENTION

The present invention relates to compounds of formula 1

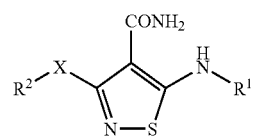

or a pharmaceutically acceptable salt, prodrug, solvate or hydrate thereof, wherein:

X is O or S;

$R^1$ is a 4–10 membered heterocyclic aromatic ring, optionally substituted with 1–4 $R^3$ groups, said $R^1$ group is optionally fused to a 4–10 membered aryl or heterocyclic group, said 4–10 membered aryl or heterocyclic groups are optionally substituted by 1 to 3 $R^3$ groups and 1 or 2 carbon atoms in the foregoing heterocyclic moiety is optionally substituted by an oxo (=O) moiety;

$R^2$ is H, $C_1$–$C_{10}$ alkyl, $C_3$–$C_{10}$ cycloalkyl, $C_2$–$C_{10}$ alkenyl, $C_2$–$C_{10}$ alkynyl, —$(CR^3R^3)_t(C_6$–$C_{10}$ aryl), or —$(CH_2)_t$ (5–10 membered heterocyclic), wherein t is an integer from 0 to 5; said alkyl group optionally includes 1 or 2 hetero moieties selected from O, S and —N($R^5$)— with the proviso that two O atoms, two S atoms, or an O and S atom are not attached directly to each other; said cycloalkyl, aryl and heterocyclic $R^2$ groups are optionally fused to a $C_6$–$C_{10}$ aryl group, a $C_5$–$C_8$ saturated cyclic group, or a 5–10 membered heterocyclic group; 1 or 2 carbon atoms in the foregoing heterocyclic moieties are optionally substituted by an oxo (=O) moiety; the —$(CH_2)_t$— moieties of the foregoing $R^2$ groups optionally include a carbon-carbon double or triple bond where t is an integer from 2 to 5, and the foregoing $R^2$ groups are optionally substituted by 1 to 5 $R^3$ groups;

each $R^3$ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —OR$^4$, —C(O)R$^4$, —C(O)OR$^4$, —NR$^5$C(O)OR$^4$, —OC(O)R$^4$, —NR$^5$SO$_2$R$^4$, —SO$_2$NR$^4$R$^5$, —NR$^5$C(O)R$^4$, —C(O)NR$^4$R$^5$, —NR$^4$R$^5$, —S(O)jR$^4$ wherein j is an integer ranging from 0 to 2, —SO$_3$H, —NR$^4$(CR$^5$R$^6$)$_t$OR$^5$, —(CH$_2$)$_t$(C$_6$–C$_{10}$ aryl), —SO$_j$(CH$_2$)$_t$(C$_6$–C$_{10}$ aryl), —S(CH$_2$)$_t$(C$_6$–C$_{10}$ aryl), —O(CH$_2$)$_t$(C$_6$–C$_{10}$ aryl), —(CH$_2$)$_t$(5–10 membered heterocyclic), and —(CR$^5$R$^6$)$_m$OR$^5$, wherein m is an integer from 1 to 5 and t is an integer from 0 to 5; said alkyl group optionally contains 1 or 2 hetero moieties selected from O, S and —N(R$^5$)— with the proviso that two O atoms, two S atoms, or an O and S atom are not attached directly to each other; said aryl and heterocyclic R$^3$ groups are optionally fused to a C$_6$–C$_{10}$ aryl group, a C$_5$–C$_8$ saturated cyclic group, or a 5–10 membered heterocyclic group; 1 or 2 carbon atoms in the foregoing heterocyclic moieties are optionally substituted by an oxo (=O) moiety; and the alkyl, aryl and heterocyclic moieties of the foregoing R$^3$ groups are optionally substituted by 1 to 3 substituents independently selected from halo, cyano, nitro, trifluoromethyl, trifluoromethoxy, azido, —NR$^5$SO$_2$R$^4$, —SO$_2$NR$^4$R$^5$, —C(O)R$^4$, —C(O)OR$^4$, —OC(O)R$^4$, —NR$^5$C(O)R$^4$, —C(O)NR$^4$R$^5$, —NR$^4$R$^5$, —(CR$^5$R$^6$)$_m$OR$^5$ wherein m is an integer from 1 to 5, —OR$^4$ and the substituents listed in the definition of R$^4$;

each R$^4$ is independently selected from H, C$_1$–C$_{10}$ alkyl, —(CH$_2$)$_t$(C$_6$–C$_{10}$ aryl), and —(CH$_2$)$_t$(5–10 membered heterocyclic), wherein t is an integer from 0 to 5; said alkyl group optionally includes 1 or 2 hetero moieties selected from O, S and —N(R$^5$)— with the proviso that two O atoms, two S atoms, or an O and S atom are not attached directly to each other; said aryl and heterocyclic R$^4$ groups are optionally fused to a C$_6$–C$_{10}$ aryl group, a C$_5$–C$_8$ saturated cyclic group, or a 5–10 membered heterocyclic group; and the foregoing R$^4$ substituents, except H, are optionally substituted by 1 to 3 substituents independently selected from halo, cyano, nitro, trifluoromethyl, trifluoromethoxy, azido, —C(O)R$^5$, —C(O)OR$^5$, —CO(O)R$^5$, —NR$^5$C(O)R$^6$, —C(O)NR$^5$R$^6$, —NR$^5$R$^6$, hydroxy, C$_1$–C$_6$ alkyl, and C$_1$–C$_8$ alkoxy; and each R$^5$ and R$^6$ is independently H or C$_1$–C$_6$ alkyl.

Preferred compounds include those of formula 1 wherein R$^1$ is a 5–6 membered nitrogen containing aromatic heterocycle ring. Specific preferred R$^1$ groups are selected from the group consisting of 3-pyrazolyl, 2-pyridyl, 3-pyridyl, 4-pyridyl, 2-pyrimidyl and 4-pyrimidyl.

Other preferred compounds include those of formula 1 wherein R$^2$ is C$_1$–C$_4$ alkyl, —(CR$^3$R$^3$)$_t$(C$_6$–C$_{10}$ aryl) or —(CH$_2$)$_t$(5–10 membered heterocyclic). In a preferred embodiment of the present invention the C$_1$–C$_4$ alkyl is methyl, ethyl or propyl substituted by a cyclohexyl group. In another preferred embodiment when R$^2$ is methyl, ethyl or propyl which are preferably substituted by —(CR$_3$R$^3$)$_t$ (C$_6$–C$_{10}$ aryl) group. Preferred R$^2$ groups include phenyl or benzyl optionally substituted by 1 to 4 substituents independently selected from halo and C$_1$–C$_4$ alkyl.

In one preferred embodiment of the present invention include compounds of formula 1 wherein R$^2$ is —(CR$^3$R$^3$)$_t$ (C$_6$–C$_{10}$ aryl). Another preferred embodiment of the present invention include compounds of formula 1 wherein R$^2$ is —C(C$_1$–C$_{10}$ alkyl)$_2$(C$_6$–C$_{10}$ aryl). A preferred embodiment of the present invention include compounds of formula 1, wherein R$^2$ is —C(H)(C$_1$–C$_{10}$ alkyl)(C$_6$–C$_{10}$ aryl). In a more preferred embodiment R$^2$ is —C(H)(C$_1$–C$_4$ alkyl)(C$_6$–C$_{10}$ aryl). In an even more preferred embodiment R$^2$ is —C(H) (C$_1$–C$_4$ alkyl)(phenyl). In a most preferred embodiment the compounds of formula 1 include those wherein R$^2$ is —C(H) (methyl)(phenyl), —C(H)(ethyl)(phenyl), or —C(H)(propyl)(phenyl). In a preferred embodiment R$^2$ is optionally substituted by 1 to 4 substituents independently selected from halo and C$_1$–C$_4$ alkyl.

Another embodiment of the present invention relates to compounds of formula 1 wherein X is S and R$^2$ is —(CR$^3$R$^3$)$_t$(C$_6$–C$_{10}$ aryl).

Other preferred compounds include those of formula 1 wherein X is S and R$^2$ is —(CH)(R$^5$)(C$_6$–C$_{10}$ aryl). Specific preferred R$^2$ groups include —(CH)(H)(C$_6$–C$_{10}$ aryl) and —(CH)(C$_1$–C$_4$ alkyl)(C$_6$–C$_{10}$ aryl)

Most preferred R$^2$ groups include chloro-benzyl.

Specific embodiments of the present invention include the following compounds:

3-Cyclohexylmethoxy-5-(pyrazin-2-ylamino)-isothiazole-4-carboxylic acid amide

3-Cyclohexylmethoxy-5-(pyrimidin-4-ylamino)-isothiazole-4-carboxylic acid amide

3-Cyclohexylmethoxy-5-(pyrimidin-2-ylamino)-isothiazole-4-carboxylic acid amide

3-Cyclohexylmethoxy-5-(3-hydroxy-pyridin-2-ylamino)-isothiazole-4-carboxylic acid amide monoformate salt 3-Cyclohexylmethoxy-5-(5-fluoro-quinazolin-4-ylamino)-isothiazole-4-carboxylic acid amide 3-cyclohexylmethoxy-5-(pyridin-2-ylamino)-isothiazole-4-carboxylic acid amide 3-Cyclohexylmethoxy-5-(3-methyl-pyridin-2-ylamino)-isothiazole-4-carboxylic acid amide 3-Cyclohexylmethoxy-5-(pyridin-3-ylamino)-isothiazole-4-carboxylic acid amide 3-Cyclohexylmethoxy-5-(pyridin4-ylamino)-isothiazole-4-carboxylic acid amide 3-Cyclohexylmethoxy-5-(2,6-dimethyl-pyrimidin-4-ylamino)-isothiazole-4-carboxylic acid amide 3-Cyclohexylmethoxy-5-(1H-pyrazol-3-ylamino)-isothiazole-4-carboxylic acid amide 5-(1H-Benzoimadazol-2-ylamino)-3-cyclohexyl-methoxy-isothiazole-4-carboxylic acid amide monoformate salt 3-(4-Chloro-benzylsulfanyl)-5-(pyridin-3-ylamino)-isothiazole-4-carboxylic acid amide 3-[1-(4-Chloro-phenyl)-propylsulfanyl]-5-(pyridin-3-ylamino)-isothiazole-4-carboxylic acid amide 3-Cyclohexylmethylsulfanyl-5-(pyridin-3-ylamino)-isothiazole-4-carboxylic acid amide 3-[1-(4-Chloro-phenyl)-ethylsulfanyl]-5-(pyridin-3-ylamino)-isothiazole-4-carboxylic acid amide 3-(4-Chloro-benzylsulfanyl)-5-(pyridin-4-ylamino)-isothiazole-4-carboxylic acid amide 3-(2-Chloro-benzylsulfanyl)-5-(pyridin-4-ylamino)-isothiazole-4-carboxylic acid amide 3-(4-Chloro-benzylsulfanyl)-5-(6-methoxy-pyridin-3-ylamino)-isothiazole-4-carboxylic acid amide 3-Hexylsulfanyl-5-(pyridin-4-ylamino)-isothiazole-4-carboxylic acid amide 3-Cyclohexylsulfanyl-5-(pyridin4-ylamino)-isothiazole-4-carboxylic acid amide 3-Phenethylsulfanyl-5-(pyridin-4-ylamino)-isothiazole-4-carboxylic acid amide 3-(4-Chloro-benzylsulfanyl)-5-(pyrimidin-4-ylamino)-isothiazole-4-carboxylic acid amide 3-(4-Chloro-benzylsulfanyl)-5-(pyrazin-2-ylamino)-isothiazole-4-carboxylic acid amide 3-(1-Phenyl-ethylsulfanyl)-5-(pyridin-3-ylamino)-isothiazole-4-carboxylic acid amide 3-(2-Chloro-benzylsulfanyl)-5-(pyridin-3-ylamino)-isothiazole-4-carboxylic acid amide 3-(3,5-Dimethoxy-benzylsulfanyl)-5-(pyridin-3-ylamino)-isothiazole-4-carboxylic acid amide 5-(Pyridin-3-ylamino)-3-(4-trifluoromethyl-benzylsulfanyl)-isothiazole-4-carboxylic acid amide 5-(Pyridin-3-ylamino)-3-(2-trifluoromethyl-benzylsulfanyl)-isothiazole-4-carboxylic acid amide 3-(1-Phenyl-propylsulfanyl)-5-(pyridin-3-ylamino)-isothiazole-4-carboxylic acid amide 3-(4-Chloro-benzylsulfanyl)-5-(pyridin-2-ylamino)-isothiazole-4-carboxylic acid amide 3-(4-Chloro-benzylsulfanyl )-5-(pyrimidin-2-ylamino)-isothiazole-4-carboxylic acid amide 3-(4-Chloro-benzylsulfanyl)-5-(6-methoxy-pyridin-2-ylamino)-isothiazole-4-carboxylic acid amide 3-[1-(4-Chloro-phenyl)-propylsulfanyl]-5-(5-methyl-pyridin-2-ylamino)-isothiazole-4-carboxylic acid amide 3-[1-(4-Chloro-phenyl)-propylsulfanyl]-5-(6-methyl-pyridin-2-ylamino)-isothiazole-4-carboxylic acid amide 3-[1-(4-Chloro-phenyl)-propylsulfanyl]-5-(3-methyl-pyridin-2-ylamino)-isothiazole-4-carboxylic acid amide 3-[1-(4-Chloro-phenyl)-propylsulfanyl]-5-(2-isopropyl-pyridin-4-ylamino)-isothiazole-4-carboxylic acid amide 3-[1-(4-Chloro-phenyl)-propysulfanyl]-5-(6-methyl-pyridin-3-ylamino)-isothiazole-4-carboxylic acid amide 3-[1-(4-Chloro-phenyl)-propylsulfanyl]-5-(pyrimidin-5-ylamino)-isothiazole-4-carboxylic acid amide and the pharmaceutically acceptable salts, prodrugs, solvates and hydrates of the foregoing compounds.

The invention also relates to a pharmaceutical composition for the treatment of a hyperproliferative disorder in a mammal which comprises a therapeutically effective amount of a compound of formula 1, or a pharmaceutically acceptable salt or hydrate thereof, and a pharmaceutically acceptable carrier. In one embodiment, said pharmaceutical composition is for the treatment of cancer such as brain, melanoma, lung, squamous cell, bladder, gastric, pancreatic, breast, head, neck, renal, prostate, colorectal, oesophageal, gynecological (such as ovarian) or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt or hydrate thereof, and a pharmaceutically acceptable carrier.

The invention also relates to a pharmaceutical composition for the prevention of blastocyte implantation in a mammal which comprises a therapeutically effective amount of a compound of formula 1, or a pharmaceutically acceptable salt or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of the compound of formula 1, or a pharmaceutically acceptable salt or hydrate thereof. In one embodiment, said method relates to the treatment of cancer such as brain, melanoma, squamous cell, bladder, gastric, pancreatic, breast, head, neck, oesophageal, prostate, colorectal, lung, renal, gynecological (such as ovarian) or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1, or a pharmaceutically acceptable salt or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula 1, or a pharmaceutically acceptable salt or hydrate thereof.

The invention also relates to a method of preventing blastocyte implantation in a mammal which comprises administering to said mammal a therapeutically effective amount of a compound of formula 1, or a pharmaceutically acceptable salt or hydrate thereof.

The invention also relates to a method of treating pain in a mammal which comprises administering to said mammal a therapeutically effective amount of a compound of formula 1, or a pharmaceutically acceptable salt or hydrate thereof.

The invention also relates to a method of treating obesity in a mammal which comprises administering to said mammal a therapeutically effective amount of a compound of formula 1, or a pharmaceutically acceptable salt or hydrate thereof.

The invention also relates to a method of treating diseases related to vasculogenesis or angiogenesis in a mammal which comprises administering to said mammal an effective amount of a compound of formula 1, or a pharmaceutically acceptable salt or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, macular degeneration, hemangioma, glioma, melanoma, Kaposi's sarcoma and ovarian, breast, lung, pancreatic, prostate, colon and epidermoid cancer.

The compounds of the present invention may be used as contraceptives in mammals.

Patients that can be treated with the compounds of formulas 1, and the pharmaceutically acceptable salts and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R)1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R)3-[4-(4-chloro-phenoxy)-benzenesulfonylamino]-tetrahydro-pyran-3-carboxylic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R)3-[4-(4-fluoro-phenoxy)-benzenesulfonylamino]-tetrahydro-furan-3-carboxylic acid hydroxyamide;

and pharmaceutically acceptable salts and solvates of said compounds.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974

(Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example CP-547,632 (Pfizer Inc., N.Y.), AG-13736 (Agouron Pharmceuticals, Inc. a Pfizer Company), SU-5416 and SU-6668 (Sugen Inc. of South San Francisco, Calif., USA), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as CP-358,774 (OSI-774) (Tarceva) (OSI Pharmaceuticals, Inc.), GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

Other anti-angiogenesis agents, including, but not limited to, other COX-II inhibitors, other M MP inhibitors, other anti-VEGF antibodies or inhibitors of other effectors of vascularization can also be used in the present invention.

The term "halo", as used herein, unless otherwise indicated, includes fluoro, chloro, bromo or iodo. Preferred halo groups are chloro.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes monovalent hydrocarbon radicals having at least one carbon-carbon double bond and also having straight, cyclic or branched moieties as provided above in the definition of "alkyl".

The term "alkynyl", as used herein, unless otherwise indicated, includes monovalent hydrocarbon radicals having at least one carbon-carbon triple bond and also having straight, cyclic or branched moieties as provided above in the definition of "alkyl".

The term "alkoxy", as used herein, unless otherwise indicated, includes 0-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

Certain compounds of formula 1 may have asymmetric centers and therefore exist in different enantiomeric forms. This invention relates to the use of all optical isomers and stereoisomers of the compounds of formula 1 and mixtures thereof. The compounds of formula 1 may also exist as tautomers. This invention relates to the use of all such tautomers and mixtures thereof.

The subject invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

DETAILED DESCRIPTION OF THE INVENTION

Compounds of the formula 1 and their pharmaceutically acceptable salts, hydrates and solvates may be prepared as described below. Unless otherwise indicated, $R^1$ and $R^2$ are as defined above.

Scheme 1:

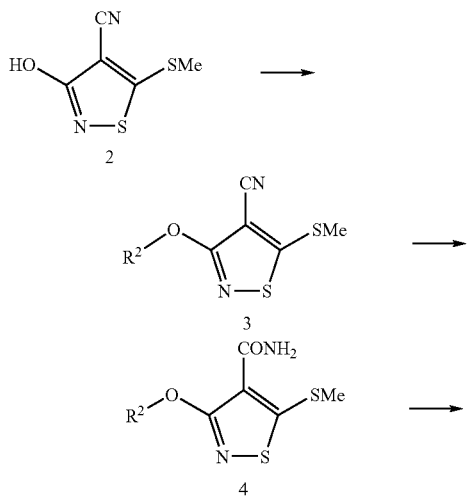

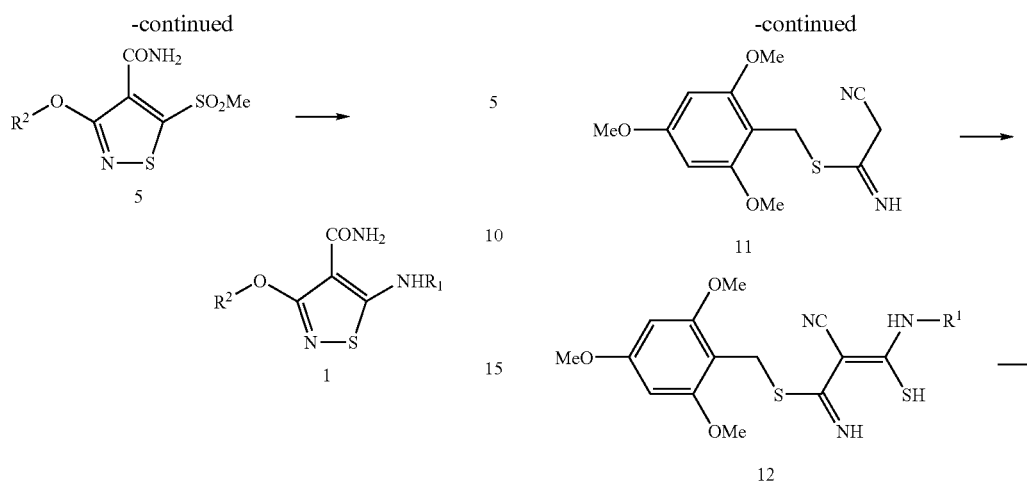
Scheme 2:
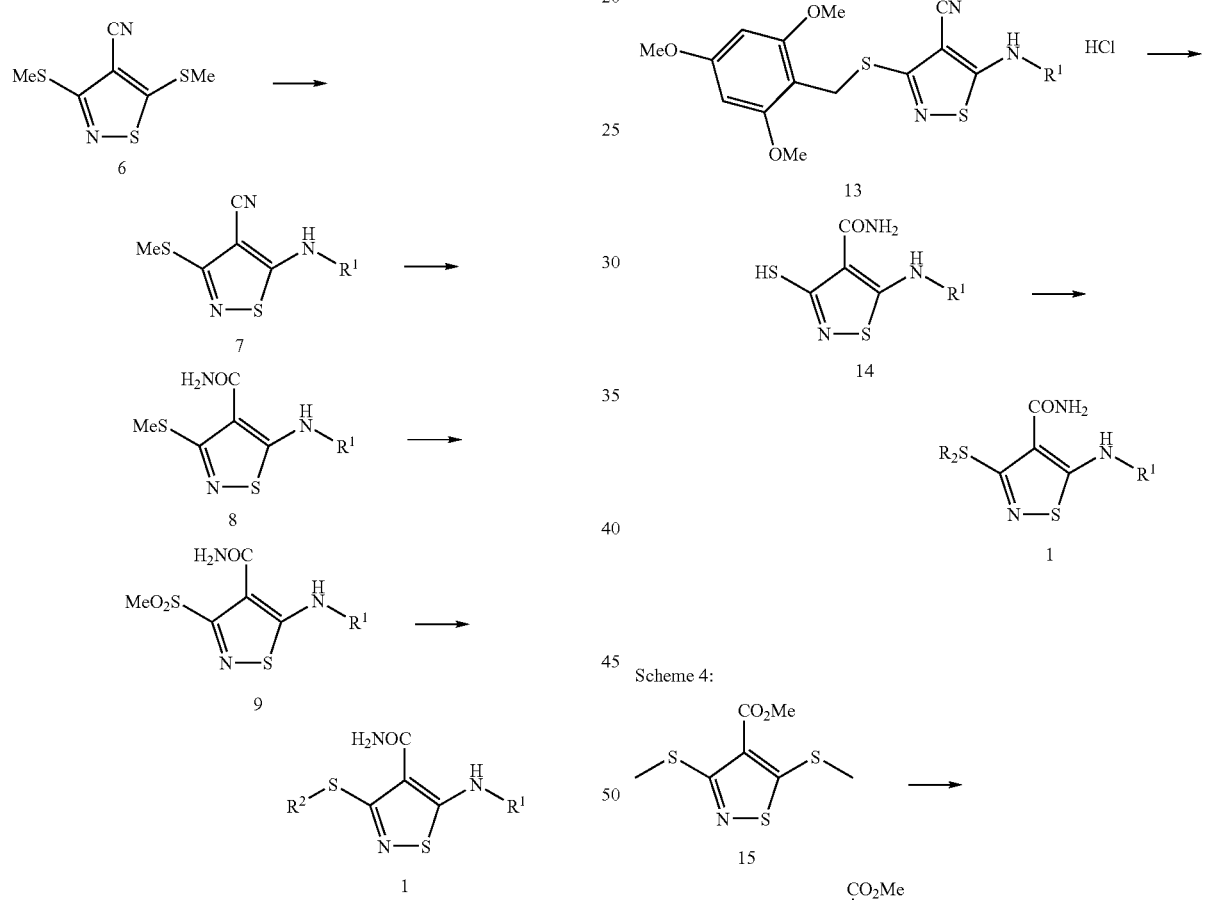
Scheme 3:
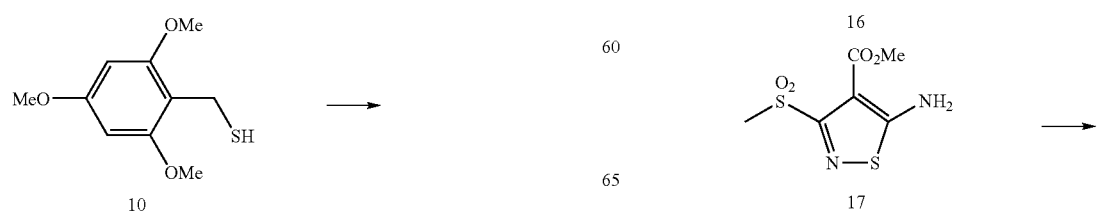

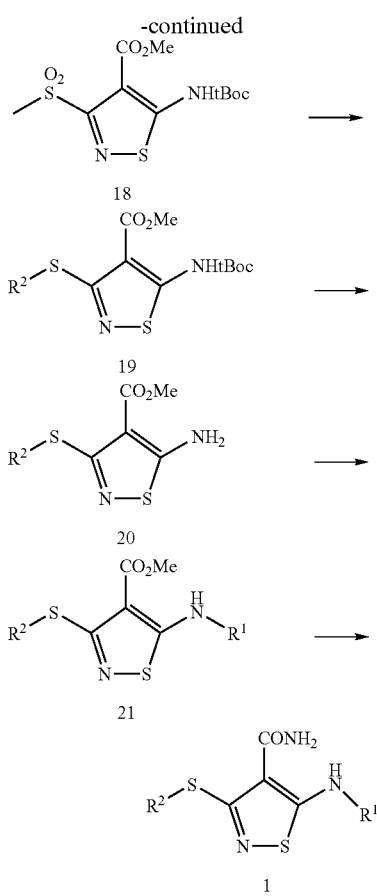

The compounds of the present invention are readily prepared by following the procedures outlined in the schemes illustrated above and typical synthetic procedures familiar to those skilled in the art.

Scheme 1 illustrates the alcohol coupling, sulfur oxidation, cyanide hydrolysis and amine addition to provide compounds of the formula 1, where X=O. In step 1 of Scheme 1, the compound of formula 3 may be prepared by treating the compound of formula 2 with an $R^2$ alcohol, a trisubstituted phosphine, preferably diphenyl-2-pyridyl phodphine, a coupling reagent, preferably diazenedicarboxylic acid bis(N'-methylpiperazide), in an aprotic polar solvent, such as THF, at a temperature ranging from −20° C. to 50° C., preferably 25° C., over a period of about 12 to 96 hours. In step 2 of Scheme 1, the compound of formula 4 may be prepared by treating the compound of formula 3 with concentrated sulfuric acid, at a temperature ranging from 0° C. to 60° C., preferably about 25° C., for a period of about 12 to 48 hours, preferably about 24 hours. In step 3 of Scheme 1, the compound of formula 5 may be prepared by treating the compound of formula 4 with an oxidizing reagent, preferably 30% hydrogen peroxide, in a polar, acidic solvent mixture, preferably acetic acid and acetic anhydride, for a period of about 12 to 96 hours, preferably about 72 hours, at a temperature ranging from 0° C. to 50° C., preferably about 25° C. In step 4 of Scheme 1, the compound of formula 1 (wherein X is 0) may be prepared by treating the compound of formula 5 with an $R^1$ amine, a strong base, preferably n-BuLi or $Cs_2CO_3$, in a polar aprotic solvent, preferably THF or DMF, for a period of about 1 to 48 hours, at a temperature ranging from 25° C. to 100° C.

Scheme 2 illustrates another method of preparing the compounds of formula 1 wherein $X^1$ is S. In step 1 of Scheme 2, the compound of formula 7 may be prepared by the addition of an $R^1$ amine, in the presence of a strong base, such as an alkoxide base, preferably sodium t-butoxide, in a polar solvent, preferably THF, for a period ranging from 12 to 96 hours at a temperature ranging from about 0° C. to 90° C., preferably 25° C. In step 2 of Scheme 2, the compound of formula 8 may be prepared by treating the compound of formula 7 with concentrated sulfuric acid, at a temperature ranging from 0° C. to 60° C., for a period of about 12 to 96 hours. In step 3 of Scheme 2 the compound of formula 9 may be prepared by treating the compound of formula 8 with an oxidizing reagent, preferably 30% hydrogen peroxide, in a polar, acidic solvent mixture, preferably acetic acid and acetic anhydride, for a period of about 12 to 96 hours, preferably about 72 hours, at a temperature ranging from 0° C. to 50° C., preferably about 25° C. In step 4 of Scheme 2, the compound of formula 1 may be prepared (wherein X is S) by treating the compound of formula 9 with a thiol of the formula $R^2SH$, with a strong base, preferably potassium t-butoxide in a polar aprotic solvent, such as THF, at a temperature ranging from 23° C. to 80° C. for a period ranging from 6 to 48 hours.

Scheme 3 illustrates a method of preparing the compounds of formula 1 wherein X is S. In step 1 of Scheme 3, the compound of formula 11 may be prepared by treating the compound of formula 10 with malonitrile, in the presence of a strong base, preferably sodium hydroxide, in a polar alcoholic solvent, such as EtOH, at a temperature ranging from 23° C. to 40° C., preferably 25° C., for a period ranging from 6 to 24 hours, preferably 4 hours. In step 2 of Scheme 3, the compound of formula 12 may be prepared by treating the compound of formula 11 with an $R^1NCS$, in a polar aprotic solvent, preferably EtOAc, at a temperature ranging from 23° C. to 80° C., preferably 60° C., for a period ranging from 6 to 48 hours. In step 3 of Scheme 3, the compound of formula 13 may be prepared by treating the compound of formula 12 with a cyclization reagent, preferably iodine, in the presence of a base, preferably pyridine, in a polar aprotic solvent, preferably EtOAc, at a temperature ranging from −20° C. to 40° C., preferably 0° C., for a period ranging from 1 to 12 hours, preferably 3 hours. In step 4 of Scheme 3, the cyanide is first hydrolyzed to the carboxamide by treating the compound of formula 13 with concentrated sulfuric acid, at a temperature ranging from 0° C. to 60° C., for a period of about 12 to 96 hours. The resulting carboxamide is not isolated, but is instead fully converted to the compound of formula 14 with the addition of a strong acid, preferably trifluoroacetic acid, a cation scavenger, preferably triethylsilane, in a non-polar solvent, preferably methylene chloride, at a temperature ranging from 0° C. to 40° C., preferably 25° C., for a period ranging from 1 to 12 hours, preferably 2 hours. In step 5 of Scheme 3, the compound of formula 1 (X=S) may be prepared by treating the compound of formula 14 with an electrophile, preferably a alkyl or benzyl halide, in the presence of a base, preferably Hunig's base, in a polar aprotic solvent, preferably DMF, at a temperature ranging from −20° C. to 40° C., preferably 25° C., for a period ranging from 1 to 24 hours.

Scheme 4 illustrates a method of preparing the compounds of formula 1 wherein X is S. In step 1 of Scheme 4, the compound of formula 16 may be prepared by treating the compound of formula 15 with an oxidizing reagent, preferably Oxone, in the presence of an acid, preferably sulfuric acid, in a polar solvent mixture, preferably water and ethanol, at a temperature ranging from −20° C. to 40° C., for a period ranging from 1 to 12 hours. In step 2 of Scheme 4, the compound of formula 17 may be prepared by treating the compound of formula 16 with ammonia, in a polar aprotic solvent system, preferably a 10:1 ratio of THF to DMF, at a temperature ranging from −20° C. to 60° C., preferably 50° C., for a period ranging from 12 to 72 hours. In step 3 of Scheme 4, the compound of formula 18 may be prepared by treating the compound of formula 17 with a protecting group electrophile, preferably t-butoxycarbonyl anhydride, in the presence of a base, preferably sodium hydride, in a polar aprotic solvent, preferably THF, at a temperature ranging from −20° C. to 40° C., preferably 25° C., for a period ranging from 1 to 12 hours, preferably 3 hours. In step 4 of Scheme 4, the compound of formula 19 may be prepared by treating the compound of formula 18 with a thiol nucleophile $R_2SH$, in the presence of a base, preferably n-BuLi, in a polar aprotic solvent, preferably THF, at a temperature ranging from −20° C. to 40° C., for a period ranging from 1 to 12 hours, preferably 3 hours. In step 5 of Scheme 4, the compound of formula 20 may be prepared by treating the compound of formula 19 with an acid, preferably trifluoroacetic acid, in a non-polar aprotic solvent, preferably methylene chloride, at a temperature ranging from −20° C. to 40° C., preferably 25° C., for a period ranging from 1 to 48 hours. In Step 6 of Scheme 4, the compound of formula 21 may be prepared by treating the compound of formula 20 with an R1 halogen, preferably an aryl bromide, in the presence of a palladium source, preferably Tris(dibenzylideneacetone)-dipalladium, in the presence of a phosphine, preferably 2,2'-Bis(diphenyl-phosphino)-1,1'-binaphthyl, in the presence of a base, preferably cesium carbonate, in a non-polar aprotic solvent, preferably toluene, at a temperature ranging from −20° C. to 120° C., preferably 100° C., for a period ranging from 1 to 72 hours. In step 7 of Scheme 4, the compound of formula 1 (X=S) may be prepared by treating the compound of formula 21 with a amine transfer reagent, preferably a mixture of trimethyl aluminum and ammonium chloride, in an aprotic solvent, preferably toluene, at a temperature ranging from −0° C. to 120° C., preferably 80° C., for a period ranging from 1 to 24 hours.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulas 1. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

Included in the present invention are compounds identical to the compounds of formula 1 but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies. Included among the radiolabelled forms of the compounds of formula 1 are the tritium and $C^{14}$ isotopes thereof.

The in vitro activity of the compounds of formula 1 in inhibiting the TrkA receptor may be determined by the following procedure.

The ability of the compounds of the present invention to inhibit tyrosine kinase activity of TrkA may be measured using a recombinant enzyme in an assay that measures the ability of compounds to inhibit the phosphorylation of the exogenous substrate, polyGluTyr (PGT, Sigma™, 4:1). The kinase domain of the human NGF/TrkA receptor is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (1.0 ug PGT per well). The final concentration of ATP in the plates is 40 uM. Test compounds are first diluted in dimethylsulfoxide (DMSO) and then serial-diluted in a 96-well plate. When added to the PGT plates, the final concentration of DMSO in the assay is 0.06%. The recombinant enzyme is diluted in phosphorylation buffer (50 mM HEPES, pH 7.4, 0.14M NaCl, 2.2 mM $MgCl_2$, 2.5 mM $MnCl_2$, 0.1 mM DTT, 0.2 mM $Na_3VO_4$). The reaction is initiated by the addition of the recombinant enzyme to the ATP and to the test compounds. After a 30 minute incubation at room temperature with shaking, the reaction is stopped with 0.5M EDTA, pH 8.0, and then aspirated. The plates are washed with wash buffer (1× imidazole wash buffer). The amount of phosphorylated PGT is quantitated by incubation with a HRP-conjugated (HRP is horseradish peroxidase)

PY-54 antibody (Transduction Labs), developed with ABTS substrate, and the reaction is quantitated on a Wallac Victor² plate reader at 405 nm. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit TrkA tyrosine kinase activity for the full length protein that exists in a cellular context, the porcine aortic endothelial (PAE) cells transfected with the human TrkA may be used. Cells are plated and allowed to attach to 96-well dishes in the same media (Ham's F12) with 10% FBS (fetal bovine serum). Test compounds, dissolved in DMSO, are serial-diluted in 96-well assay blocks with serum free media containing 0.1% fatty-acid free bovine serum albumin (BSA). The cells are then washed, re-fed with serum free media with and without test compounds, and allowed to incubate for 2 hr. At the end of the 2 hr. incubation, NGF (150 ng/ml final) is added to the media for a 10 minute incubation. The cells are washed and lysed in Tris-lysis buffer (50 mM Tris, pH 7.4, 150 mM NaCl, 1% NP-40, 10% glycerol, 2mM $Na_3VO_4$, 0.5 mM EDTA, complete protease inhibitor cocktail tablets without EDTA). TBS is used as a diluter solution to mix the cell lysates. The extent of phosphorylation of TrkA is measured using an ELISA assay. The black, Maxisorb 96-well plates are custom-coated with goat anti-rabbit antibody (Pierce). The Trk(C-14)sc-11 antibody (Santa Cruz) at 0.4 µg/well is bound to the plates for 2 hr. in SuperBlock Blocking Buffer in TBS (Pierce). Any unbound antibody is washed off the plates prior to addition of the cell lysate. After a 2 hr. incubation of the lysates with the Trk(C-14)sc-11 antibody, the TrkA associated phosphotyrosine is quantitated by development with the HRP-conjugated PY54 antibody and SuperSignal ELISA Femto substrate (Pierce). The ability of the compounds to inhibit the NGF-stimulated autophosphorylation reaction by 50%, relative to NGF-stimulated controls, is reported as the $IC_{50}$ value for the test compound.

The in vitro activity of the compounds of formula 1 in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 µg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 µM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, $VEGF_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenylmethylsulfonyl fluoride), 1 µg/ml pepstatin, 1 µg/ml leupeptin, 1 µg/ml aprotinin, 2 mM sodium pyrophosphate, 2 mM sodium orthovanadate). The extent of phosphorylation of KDR is measured using an ELISA assay. The 96-well plates are coated with 1 µg per well of goat anti-rabbit antibody. Unbound antibody is washed off the plate and remaining sites are blocked with Superblock buffer (Pierce) prior to addition of the anti-flk-1 C-20 antibody (0.5 µg per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

The ability of the compounds to inhibit mitogenesis in human endothelial cells is measured by their ability to inhibit ³H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, $10^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2–30 ng/ml $VEGF_{165}$. During the last 3 hours of the 24 hour compound treatment, the cells are pulsed with ³H thymidine (NEN, 1 µCi per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of ³H thymidine incorporation is measured by scintillation counting. The ability of the compounds to inhibit incorporation by 50%, relative to control (VEGF treatment with DMSO vehicle only) is reported as the IC50 value for the test compound.

It has also been found that compounds of the present invention are also inhibitors of the receptor tyrosine kinases, VEGF-2 and the related Trk family member TrkB.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred antimetabolites disclosed in European Patent Application No. 239362 such as N-(5-[N-(3,4-dihydro-2-methyl4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing those compounds. It is to be understood that the scope of the present invention is not limited in any way by the scope of the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Where preparative HPLC chromatography is referred to in the preparations and examples below, the general conditions used, unless otherwise indicated, are as follows: A Symmetry C8 reverse phase 19×50 mm column is used with a 5 μm pore size. The flow rate is 18 mL/min. and a column gradient of 5% acetonitrile/ water to 100% acetonitrile is used, always with 0.1% formic acid present.

In the following examples and preparations, "Et" means ethyl, "Ac" means acetyl, "Me" means methyl, "THF" means tetrahydrofuran, and "Bu" means butyl.

Preparation 1

3-Cyclohexylmethoxy-5-methylsulfanyl-isothiazole-4-carbonitrile (3): 3-hydroxy-5-methylsulfanyl-isothiazole-4-carbonitrile (10 g, 58 mmol) is dissolved in anhydrous THF (200 mL). Cyclohexylmethanol (11 mL, 87.1 mmol) and diphenyl-2-pyridyl-phosphine (30.5 g, 116 mmol) are added to the solution. Diazenedicarboxylic acid bis(N'-methylpiperazide) (32.7 g, 116 mmol) is slurried in anhydrous THF (200 mL) and added dropwise over 1 hour to the reaction. The reaction is stirred at room temp. for 3 days and then diluted with water and extracted with EtOAc (100 mL×3). The combined organics are then dried over magnesium sulfate, filtered and concentrated in vacuo. Chromatography (20% EtOAc/hexane) followed by a second chromatography (10% EtOAc/hexane) provides 3 (7.3 g, 52%). $^1$H NMR (d$_6$ DMSO): δ 4.18 (2H, d, J=6.3 Hz), 2.76 (3H, s), 1.64–1.81 (6H, m), 1.16–1.27 (3H, m), 1.00–1.13 (2H, m).

3-Cyclohexylmethoxy-5-methylsulfanyl-isothiazole-4-carboxylic acid amide (5): 3-Cyclohexylmethoxy-5-methylsulfanyl-isothiazole-4-carbonitrile (3) (6.3 g, 23.5 mmol) is dissolved in conc. sulfuric acid (31.5 mL) and stirred at room temperature for 24 hrs. Ice was added and the resulting suspension was filtered and washed with water and then washed with 1N NaOH. The solids were dried in vacuo to obtain crude 3-cyclohexylmethoxy-5-methylsulfanyl-isothiazole-4-carboxylic acid amide (4, 8.7 g). This solid is slurried in acetic acid (37 mL) and acetic anhydride (37 mL). Hydrogen peroxide (30%, 18.5 mL) is then added and the reaction is stirred at room temperature for 18 hours. More hydrogen peroxide (30%, 18.5 mL) is then added and the reaction is stirred at room temperature for 3 days. Water is then added and the suspension is filtered and the solids are further dried in vacuo to provide 5 (5.06 g, 62%). $^1$H NMR ($d_6$ DMSO): δ 7.97 (1H, s), 7.87 (1H, s), 4.14 (2H, d, J=6.0 Hz), 3.54 (3H, s), 1.59–1.78 (6H, m), 1.09–1.25 (3H, m), 0.94–1.03 (2H, m); LRMS (M+): 318.9.

Method A: Synthesis of 5-(1H-Benzoimadazol-2-ylamino)-3-cyclohexylmethoxy-isothiazole-4-carboxylic acid amide monoformate salt: 3-Cyclohexylmethoxy-5-methylsulfanyl-isothiazole-4-carboxylic acid amide (5) (30 mg, 0.094 mmol) is dissolved in DMF (0.3 mL) and the solution is agitated on a shaker plate. 1H-Benzoimidazol-2-ylamine (25 mg, 0.188 mmol) and cesium carbonate (61 mg, 0.188 mmol) are then added and the reaction mixture is heated to 100° C. and agitated for 4 hrs. The resulting solution is then filtered and the mother liquor is purified by preparative HPLC to provide 5-(1H-Benzoimidazol-2-ylamino)-3-cyclohexylmethoxy-isothiazole-4-carboxylic acid amide monoformate salt (1.0 mg). $^1$H NMR ($d_6$ DMSO): δ 12.09 (1H, s), 11.88 (1H, s), 7.77 (1H, s), 7.45–7.47 (1H, m), 7.36–7.38 (1H, m), 7.05–7.10 (2H, m), 7.01 (1H, s), 4.19 (2H, d, J=6.4 Hz), 1.61–1.83 (6H, m), 1.14–1.31 (3H, m), 0.97–1.11 (2H, m); LRMS (M+): 372.1.

Method B: Synthesis of: 3-cyclohexylmethoxy-5-(pyridin-2-ylamino)-isothiazole-4-carboxylic acid amide: 2-aminopyridine (30 mg, 0.314 mmol) is dissolved in THF (3 mL) and n-BuLi (2.5 M, 0.126 mL, 0.314 mmol) is added dropwise at room temp. After 1 hour, 3-Cyclohexylmethoxy-5-methylsulfanyl-isothiazole-4-carboxylic acid amide (5) (50 mg, 0.157 mmol) is added. After 1 day the reaction is diluted with water and extracted with EtOAc (5 mL×3). The combined organics are dried over sodium sulfate, filtered and concentrated in vacuo. The resulting solid was purified by prep HPLC to provide 3-cyclohexylmethoxy-5-(pyridin-2-ylamino)-isothiazole-4-carboxylic acid amide (1.0 mg). $^1$H NMR ($d_6$ DMSO): δ 11.79 (1H, s), 8.42 (1H, d, J=7 Hz), 7.79–7.85 (1H, m), 7.72 (1H, s), 7.39 (1H, d, J=14 Hz), 7.04–7.08 (2H, m), 4.21 (2H, d, J=11.0 Hz), 1.70–1.80 (6H, m), 1.03–1.36 (5H, m); LRMS (M+): 333.0.

Preparation 2

3-Methylsulfanyl-5-(pyridin-4-ylamino)-isothiazole-4-carbonitrile (7): 4-aminopyridine (930 mg, 9.9 mmol) is dissolved in anhydrous THF (30 mL) and potassium tertbutoxide (1.11 g, 9.9 mmol) is added. The resulting solution is stirred for 1 hour at room temperature. 3,5-Bis-methylsulfanyl-isothiazole-4-carbonitrile (6) (1.0 g, 4.94 mmol) is added and the reaction is stirred for 3 days. Ammonium chloride (173 mg, 9.9 mmol) is added and the resulting suspension is stirred at room temperature for 30 min. A small amount of water is added and the solution is filtered. The mother liquor is concentrated in vacuo. Chromatography (5% MeOH/methylene chloride) provides 7 (1.0g, 81%). $^1$H NMR ($d_6$ DMSO): δ 8.29 (2H, broad s), 7.04 (2H, broad s), 2.60 (3H, s).

3-Methylsulfanyl-5-(pyridin-4-ylamino)-isothiazole-4-carboxylic acid amide (8): Compound 7 (1.0 g, 4.0 mmol) is dissolved in sulfuric acid (5 mL). The resulting solution is stirred at room temperature for 2 hours, heated to 50° C. for 3.5 hours, then at room temperature for 18 hours, then heated to 50° C. for 1 hour. The reaction was then cooled to room temperature and 1N NaOH (5 mL) was added. The resulting solids were filtered and washed with saturated aqueous sodium bicarbonate to provide 8 (1.15 g, 4.0 mmol). $^1$H NMR ($d_6$ DMSO): δ 8.12 (2H, d, J=5.8 Hz), 6.78 (2H, d, J=5.8 Hz), 2.32 (3H, s); LRMS (M+): 267.0, (M−): 265.0.

3-(4-Chloro-benzylsulfanyl)-5-(pyridin-4-ylamino)-isothiazole-4-carboxylic acid amide: Compound 8 (500 mg, 1.88 mmol) is slurried in acetic anhydride (1.25 mL) and acetic acid (1.25 mL). Hydrogen peroxide (30%, 0.532 mL, 4.7 mmol) is added and stirred for 1 hour. Additional hydrogen peroxide (30%, 0.532 mL, 4.7 mmol) is then added and the reaction is stirred for 1 hour. Water (about 15 mL) is added and the solids were filtered and further dried in vacuo. These solids were determined to be mainly 3-Methanesulfinyl-5-(pyridin-4-ylamino)-isothiazole-4-carboxylic acid amide. The solids are thus re-combined with the mother liquor and acetic anhydride (2.0 mL), acetic acid (2.0 mL) and hydrogen peroxide (30%, 2 mL) are added and stirred for 18 hours at room temperature. The reaction was then extracted with ethyl acetate (15 mL×3) and the combined organics were dried over sodium sulfate, then filtered and concentrated in vacuo obtain crude 3-Methanesulfonyl-5-(pyridin-4-ylamino)-isothiazole-4-carboxylic acid amide (9) (170 mg).

Potassium tertbutoxide (318 mg, 2.84 mmol) is dissolved in anhydrous THF (5 mL) and (4-Chlorophenyl)-methanethiol (0.375 mL, 2.84 mmol) is then added and stirred for 30 min room temperature. This resulting solution is then added to a solution of crude 9 (170 mg) dissolved in anhydrous THF (3 mL). The reaction is stirred for 4 hours at room temperature and then heated to 60° C. for 18 hours. The reaction is diluted with water and extracted with a solution containing 5% methanol and 95% methylene chloride (10 mL×3). The combined organics are dried over sodium sulfate, filtered and then concentrated in vacuo. Chromatography (3% MeOH/methylene chloride) provides 3-(4-Chloro-benzylsulfanyl)-5-(pyridin-4-ylamino)-isothiazole-4-carboxylic acid amide (18 mg, 2.5%-2 steps). $^1$H NMR ($d_6$ DMSO): δ 8.17 (2H, broad s), 7.45 (2H, d, J=8.4 Hz), 7.37 (2H, d, J=8.4 Hz), 6.99 (2H, broad s), 4.32 (2H, s); LRMS (M+): 376.9, (M−): 375.0.

Preparation 3

2-Cyano-thioacetimidic acid 2,4,6-trimethoxy-benzyl ester (11): To a solution of NaOH (373 mg, 9.4 mmol) in water (11 mL) and ethanol (11 mL) is added (2,4,6-Trimethoxy-phenyl)-methanethiol (10) (2 g, 9.4 mmol) at room temperature. Malonitrile (0.588 mL, 9.4 mmol) is then added and the suspension is cooled to 0° C. After 4 hours, saturated aqueous ammonium chloride (14.6 mL) is added and the suspension is filtered. The solids are washed with ether and then hexane. The solid is collected and further dried in vacuo to provide 13 as a white solid (1.57 g, 60%). $^1$H NMR ($d_6$ DMSO): δ 6.78 (2H, br. s), 6.25 (2H, s), 3.98 (2H, s), 3.79 (6H, s), 3.78 (3H, s).

2-Cyano-3-mercapto-3-(pyridin-3-ylamino)-thioacrylimidic acid 2,4,6-trimethoxy-benzyl ester (12): To compound 11 (6.76 g, 24.1 mmol) in ethyl acetate (18 mL) is added 3-pyridylisothiocyanate (3.9 ml·, 36.2 mmol) at room temperature. The reaction is then heated to 60° C. and stirred for 4 hours. More ethyl acetate is added (12 mL) and the reaction is stirred for an additional 4 hours. The reaction is cooled to room temperature and filtered. The solids are washed with ethyl ether twice and with methanol once. The solids are further dried in vacuo to obtain compound 12 (5.88 g, 59%). $^1$H NMR (d$_6$ DMSO): δ 10.12 (1H, br. s), 8.46 (1H, d, J=2.4 Hz), 8.36 (1H, d, J=5.2 Hz), 7.71 (1H, d, J=9.0 Hz), 7.37 (1H, dd, J=9.0, 5.2 Hz), 6.27 (2H, s), 4.25 (2H, s), 3.81 (6H, s), 3.77 (3H, s).

5-(Pyridin-3-ylamino)-3-(2,4,6-trimethoxy-benzylsulfanyl)-isothiazole-4-carbonitrile hydrochloride salt (13): To compound 12 (5.88 g, 14.1 mmol) in ethyl acetate (127 mL) is added pyridine (2.3 mL, 28.3 mmol) at 0° C. A solution of iodine (3.6 g, 14.1 mmol) in ethyl acetate (178 mL) is then added over 2 hours to the reaction. The reaction is then stirred for an additional 3 hours at 0° C. 1N HCl (101.5 mL) is then added and stirred for 5 min. The suspension is then filtered and washed with water to provide 13 (2.53 g, 40%). The mother liquor is basified with saturated aqueous sodium bicarbonate and more ethyl acetate is added (200 mL). The layers are separated and the organic layer is filtered and the mother liquor is concentrated in vacuo. To the resulting solids are added ethyl acetate (183 mL) and 1N HCl (61 mL) and the suspension is stirred for 5 minutes. Filtration provides additional 13 (1.21 g, 19%). $^1$H NMR (d$_6$ DMSO): δ 11.27 (1H, br. s), 8.72 (1H, d, J=2.1 Hz), 8.49 (1H, dd, J=4.9, 1 Hz), 8.05 (1H, dd, J=8.4, 2.1 Hz), 7.74 (1H, dd, J=8.4, 4.9 Hz), 6.23 (2H, s), 4.35 (2H, s), 3.76 (9H, s).

3-Mercapto-5-(pyridin-3-ylamino)-isothiazole-4-carboxylic acid amide (14): Compound 13 (2.74 g, 6.1 mmol) is dissolved in sulfuric acid (32 mL) and the reaction is stirred for 2 days at room temperature. Water (0.11 mL, 6.1 mmol) is then added and the reaction is stirred for one additional day. The reaction is filtered and washed with water. The red solids are further dried in vacuo to provide 2.26 g of crude material. This material is dissolved methylene chloride (27 mL) and trifluoro acetic acid (3 mL). Triethylsilane is then added at room temperature and the reaction is stirred for 2 hours. Methanol (1.9 mL) is added to the mixture and the resulting suspension was filtered to provide 15 (1.63 g). Additional methanol (1.9 mL) is added to the mother liquor and this suspension is re-filtered to provide additional 14 (60 mg, 73% total, 2 steps). $^1$H NMR (d$_6$ DMSO): δ 12.26 (1H, br. s), 9.86 (1H, s), 8.72 (1H, d, J=2.4 Hz), 8.51 (1H, dd, J=4.8, 0.8 Hz), 7.97 (1H, d, J=8 Hz), 7.66 (1H, dd, J=8, 4.8 Hz). LRMS (M+): 253.0, (M−): 251.0.

3-(4-Chloro-benzylsulfanyl)-5-(pyridin-3-ylamino)-isothiazole-4-carboxylic acid amide: Compound 14 (50 mg, 0.14 mmol) is dissolved in DMF (0.15 mL) and Hunig's base is added (0.048 mL, 0.27 mmol) followed by 4-chlorobenzyl chloride (22 mg, 0.14 mmol) at room temperature. The reaction is stirred for 1 hour and then water (0.2 mL) is added and the resulting solids are filtered and washed with water and then methylene chloride to provide 3-(4-Chlorobenzylsulfanyl)-5-(pyridin-3-ylamino)-isothiazole-4-carboxylic acid amide (25.7 mg, 49%). $^1$H NMR (d$_6$ DMSO): δ 10.37 (1H, br. s), 8.51 (1H, d, J=2.8 Hz), 8.26 (1H, d, J=4.4 Hz), 7.61–7.64 (1H, m), 7.42 (2H, d, J=8 Hz), 7.38–7.41 (1H, m), 7.33 (2H, d, J=8 Hz), 4.40 (2H, s). LRMS (M+): 376.9, (M−): 374.9.

Preparation 4

3,5-Bis-methanesulfonyl-isothiazole-4-carboxylic acid methyl ester (16): Oxone (446.3 g, 0.73 mol) is slurried in EtOH (150 mL) and water (850 mL). 3,5-Bis-methylsulfanyl-isothiazole-4-carboxylic acid methyl ester (15) (28.5 g, 0.121 mol) is added. The reaction is cooled to 0° C. and sulfuric acid (290 mL) is added dropwise over 1.5 hrs. The reaction is then warmed to room temperature and stirred for 14 hrs. The reaction is then filtered and washed with copious amounts of water to provide 16 (33.1 g, 92%) as a white solid. $^1$H NMR (d$_6$ DMSO): δ 3.90 (3H, s), 3.60 (3H, s), 3.44 (3H, s).

5-Amino-3-methanesulfonyl-isothiazole-4-carboxylic acid methyl ester (17): In a 3 neck flask fitted with a condenser, compound 16 (1 g, 3.33 mmol) is dissolved in THF (20 mL) and DMF (2 mL) and warmed to 50° C. Ammonia gas is then bubbled into the reaction mixture for 16 hrs. The solvent is then removed in vacuo to provide a crude solid. Water is added to the solid and the mixture is then filtered and washed with water (2×) followed by methylene chloride (5 mL×2) to provide 17 (588 mg, 75%) as a yellow powder. $^1$H NMR (d$_6$ DMSO): δ 8.11 (2H, br. s), 3.74 (3H, s), 3.30 (3H, s). LRMS (M+): 237.1, (M−): 235.0.

5-tert-Butoxycarbonylamino-3-methanesulfonyl-isothiazole-4-carboxylic acid methyl ester (18): Compound 17 (6.64 g, 28.1 mmol) is dissolved in THF (70 mL). NaH (60%, 1.70 g, 42.15 mmol) is then added slowly in three equal portions to the reaction. After 30 min., a solution of t-butoxycarbonyl anhydride (9.2 g, 42.15 mmol) in THF (30 mL) is added dropwise to the reaction over 10 min. After 2 hrs., the reaction was diluted carefully with water and extracted with ethyl acetate (3×35 mL). The combined organics were rinsed with brine and then dried over sodium sulfate. The suspension was then filtered and the solvent was evaporated. Column chromatography (20%→50% EtOAc/Hexane) provided 18 (6.5 g 69%) as a white solid. $^1$H NMR (d$_6$ DMSO): δ 11.20 (1H, br. s), 3.80 (3H, s), 3.35 (3H, s), 1.50 (9H, s).

5-tert-Butoxycarbonylamino-3-(4-chloro-benzylsulfanyl)-isothiazole-4-carboxylic acid methyl ester (19): To a solution of n-BuLi (2.5M, 11.5 mL, 28.8 mmol) in THF (20 mL) at 0° C. is added (4-Chloro-phenyl)-methanethiol (4 mL, 30 mmol) dropwise over 15 min. After 1 hr., a solution of 18 (2 g, 6 mmol) in THF (15 mL) is added. The reaction is then stirred at 0° C. for 1 hour and 2 hrs. at room temperature. The reaction was then quenched with water and extracted with EtOAc (3×50 mL). The combined organics are then washed with brine, dried over sodium sulfate, filtered and concentrated in vacuo. Column chromatography (3% EtOAc/hexane) provides 19 (1.98 g, 80%) as a white solid. $^1$H NMR (CDCl$_3$): δ 10.00 (1H, br. s), 7.29 (2H, d, J=8.4 Hz), 7.25 (2H, d, J=8.4 Hz), 4.36 (2H, s), 3.89 (3H, s), 1.53 (9H, s).

5-Amino-3-(4-chloro-benzylsulfanyl)-isothiazole-4-carboxylic acid methyl ester (20): Compound 19 (6.5 g, 15.67 mmol) is dissolved in methylene chloride (65 mL) and TFA is added (65 mL). After 16 hrs., the reaction is filtered and the solids are washed with ethyl ether. The solids are further dried in vacuo to provide 20 (4.06 g, 82%). $^1$H NMR (d$_6$ DMSO): δ 7.88 (2H, br. s), 7.38 (2H, d, J=8.6 Hz), 7.32 (2H, d, J=8.6 Hz), 4.24 (2H, s), 3.69 (3H, s).

3-(4-Chloro-benzylsulfanyl)-5-(pyrimidin-2-ylamino)-isothiazole-4-carboxylic acid methyl ester (21): racemic 2,2'-Bis(diphenyl-phosphino)-1,1'-binaphthyl (87 mg, 0.14 mmol) is dissolved in toluene (4.5 mL) and then Tris (dibenzylideneacetone)-dipalladium (0) (44 mg, 0.05 mmol), Cesium carbonate (468 mg, 1.43 mmol), 2-bromopyrimidine (228 mg, 1.43 mmol), and compound 20 (300 mg, 0.96 mmol) are added. The reaction mixture is vigorously stirred at 100° C. for 4 hrs. The reaction is then filtered hot and washed with methylene chloride followed by hot dichloroethane (30 mL). The mother liquor is then concentrated in vacuo and triturated with MeOH to obtain a crude solid which is recrystalized from dichloroethane to provide 21 (265 mg, 71%). $^1$H NMR (d$_6$ DMSO): δ 10.72 (1H, s), 8.79 (2H, d, J=5.0 Hz), 7.44 (2H, d, J=8.2 Hz), 7.34 (2H, d, J=8.2 Hz), 7.23 (1H, dd, J=5.0, 5.0 Hz), 4.35 (2H, s), 3.86 (3H, s).

3-(4-Chloro-benzylsulfanyl)-5-(pyrimidin-2-ylamino)-isothiazole-4-carboxylic acid amide: Trimethyl aluminum (2M/toluene, 2.55 mL, 5.1 mmol) is added to a dry flask containing ammonium chloride (272.3 mg, 5.1 mmol). The solution is then allowed to stir for 30 min and is added to a dry flask containing compound 21 (100 mg, 0.26 mmol). The reaction is then heated to 80° C. for 4 hours and then cooled to room temperature. The reaction is then carefully quenched with 1 N HCl and extracted with EtOAc (×3). The combined organics are dried over sodium sulfate, filtered and concentrated in vacuo. Column chromatography (20%→50% EtOAc/methylene chloride) provides 3-(4-Chloro-benzylsulfanyl)-5-(pyrimidin-2-ylamino)-isothiazole-4-carboxylic acid amide (16.2 mg, 17%) in addition to the starting material 21 (36.6 mg). $^1$H NMR (d$_6$ DMSO): δ 11.61 (1H, br. s), 8.73 (2H, d, J=5.0 Hz), 7.43 (2H, d, J=8.4 Hz), 7.34 (2H, d, J=8.4 Hz), 7.15 (1H, dd, J=5.0, 5.0 Hz), 4.46 (2H, s). LRMS (M+): 378.1, (M−): 376.0.

The following examples were prepared using the methods described above. HPLC method A refers to the following conditions: A Polaris 5 micron C18-A 20×2.0 mm column made by Metachem Technologies is utilized with a 1 mL/min. flow rate, and the following solvent gradient:

| Solvent A/B | Time (min.) |
|---|---|
| 95/5 | 0 min. |
| 80/20 | 1.25 |

-continued

| Solvent A/B | Time (min.) |
|---|---|
| 50/50 | 2.50 |
| 0/100 | 3.75 |
| 0/100 | 4.10 (finished) |

Solvent A contains equal parts of acetonitrile and water with 0.01% formic acid, and solvent B contains acetonitrile with 0.005% formic acid. HPLC method B refers to the following conditions: The column used is a ZORBAX™ RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 ml/minute. HPLC method C refers to the following conditions: A Symmetry C8 reverse phase 19×50 mm column is used with a 5 □m pore size. The flow rate is 25 mL/min. and a linear column gradient of 5% acetonitrile/water to 100% acetonitrile, always with 0.1% formic acid present is used with a 15 min. total run time.

TABLE I

| Example No. (preparation #) | Name | LRMS (M+) | HPLC retention time (min) | HPLC Method |
|---|---|---|---|---|
| 1 (preparation #1) | 3-Cyclohexylmethoxy-5-(pyrazin-2-ylamino)-isothiazole-4-carboxylic acid amide | 334 | 2.5 | A |
| 2 (preparation #1) | 3-Cyclohexylmethoxy-5-(pyrimidin-4-ylamino)-isothiazole-4-carboxylic acid amide | 334 | 2.3 | A |
| 3 (preparation #1) | 3-Cyclohexylmethoxy-5-(pyrimidin-2-ylamino)-isothiazole-4-carboxylic acid amide | 334 | 2.3 | A |
| 4 (preparation #1) | 3-Cyclohexylmethoxy-5-(3-hydroxy-pyridin-2-ylamino)-isothiazole-4-carboxylic acid amide monoformate salt | 348.9 | 9.98 | C |
| 5 (preparation #1) | 3-Cyclohexylmethoxy-5-(5-fluoro-quinazolin-4-ylamino)-isothiazole-4-carboxylic acid amide | 401.9 | 2.8 | A |
| 6 (preparation #1) | 3-cyclohexylmethoxy-5-(pyridin-2-ylamino)-isothiazole-4-carboxylic acid amide | 333 | 2.7 | A |
| 7 (preparation #1) | 3-Cyclohexylmethoxy-5-(3-methyl-pyridin-2-ylamino)-isothiazole-4-carboxylic acid amide | 347 | 2.8 | A |
| 8 (preparation #1) | 3-Cyclohexylmethoxy-5-(pyridin-3-ylamino)-isothiazole-4-carboxylic acid amide | 333 | 2.3 | A |
| 9 (preparation #1) | 3-Cyclohexylmethoxy-5-(pyridin-4-ylamino)-isothiazole-4-carboxylic acid amide | 333 | 1.7 | A |
| 10 (preparation #1) | 3-Cyclohexylmethoxy-5-(2,6-dimethyl-pyrimidin-4-ylamino)-isothiazole-4-carboxylic acid amide | 362 | 2.2 | A |
| 11 (preparation #1) | 3-Cyclohexylmethoxy-5-(1 H-pyrazol-3-ylamino)-isothiazole-4-carboxylic acid amide | 322 | 2.1 | A |
| 12 (preparation #1) | 5-(1H-Benzoimadazol-2-ylamino)-3-cyclohexylmethoxy-isothiazole-4-carboxylic acid amide monoformate salt | 370 (M−) | 11.64 | C |

TABLE I-continued

| Example No. (preparation #) | Name | LRMS (M+) | HPLC retention time (min) | HPLC Method |
|---|---|---|---|---|
| 13 (preparation #3) | 3-(4-Chloro-benzylsulfanyl)-5-(pyridin-3-ylamino)-isothiazole-4-carboxylic acid amide (16) | 377.0 | 2.2 | A |
| 14 (preparation #3) | 3-[1-(4-Chloro-phenyl)-propylsulfanyl]-5-(pyridin-3-ylamino)-isothiazole-4-carboxylic acid amide | 404.8 | 2.5 | B |
| 15 (preparation #3) | 3-Cyclohexylmethylsulfanyl-5-(pyridin-3-ylamino)-isothiazole-4-carboxylic acid amide | 349.0 | 2.5 | A |
| 16 (preparation #3) | 3-[1-(4-Chloro-phenyl)-ethylsulfanyl]-5-(pyridin-3-ylamino)-isothiazole-4-carboxylic acid amide | 391.0 | 2.3 | A |
| 17 (preparation #2) | 3-(4-Chloro-benzylsulfanyl)-5-(pyridin-4-ylamino)-isothiazole-4-carboxylic acid amide | 377 | 6.69 | B |
| 18 (preparation #2) | 3-(2-Chloro-benzylsulfanyl)-5-(pyridin-4-ylamino)-isothiazole-4-carboxylic acid amide | 377.0 | 1.6 | A |
| 19 (preparation #3) | 3-(4-Chloro-benzylsulfanyl)-5-(6-methoxy-pyridin-3-ylamino)-isothiazole-4-carboxylic acid amide | 407.2 | 2.6 | A |
| 20 (preparation #2) | 3-Hexylsulfanyl-5-(pyridin-4-ylamino)-isothiazole-4-carboxylic acid amide | 337 | 8.46 | B |
| 21 (preparation #2) | 3-Cyclohexylsulfanyl-5-(pyridin-4-ylamino)-isothiazole-4-carboxylic acid amide | 335 | 7.4 | B |
| 22 (preparation #2) | 3-Phenethylsulfanyl-5-(pyridin-4-ylamino)-isothiazole-4-carboxylic acid amide | 357 | 1.5 | A |
| 23 (preparation #2) | 3-(4-Chloro-benzylsulfanyl)-5-(pyrimidin-4-ylamino)-isothiazole-4-carboxylic acid amide | 375.7 (M−) | 2.4 | A |
| 24 (preparation #2) | 3-(4-Chloro-benzylsulfanyl)-5-(pyrazin-2-ylamino)-isothiazole-4-carboxylic acid amide | 378.1 | 5.04 | C |
| 25 (preparation #3) | 3-(1-Phenyl-ethylsulfanyl)-5-(pyridin-3-ylamino)-isothiazole-4-carboxylic acid amide | 354.9 (−) | 2.5 | A |
| 26 (preparation #3) | 3-(2-Chloro-benzylsulfanyl)-5-(pyridin-3-ylamino)-isothiazole-4-carboxylic acid amide | 377.2 | 2.5 | A |
| 27 (preparation #3) | 3-(3,5-Dimethoxy-benzylsulfanyl)-5-(pyridin-3-ylamino)-isothiazole-4-carboxylic acid amide | 403.1 | 2.0 | A |
| 28 (preparation #3) | 5-(Pyridin-3-ylamino)-3-(4-trifluoromethyl-benzylsulfanyl)-isothiazole-4-carboxylic acid amide | 411.1 | 2.7 | A |
| 29 (preparation #3) | 5-(Pyridin-3-ylamino)-3-(2-trifluoromethyl-benzylsulfanyl)-isothiazole-4-carboxylic acid amide | 411.1 | 2.6 | A |
| 30 (preparation #3) | 3-(1-Phenyl-propylsulfanyl)-5-(pyridin-3-ylamino)-isothiazole-4-carboxylic acid amide | 371.2 | 2.2 | A |
| 31 (preparation #4) | 3-(4-Chloro-benzylsulfanyl)-5-(pyridin-2-ylamino)-isothiazole-4-carboxylic acid amide | 377.2 | 2.3 | A |
| 32 (preparation #4) | 3-(4-Chloro-benzylsulfanyl)-5-(pyrimidin-2-ylamino)-isothiazole-4-carboxylic acid amide | 378.1 | 2.9 | A |
| 33 (preparation #4) | 3-(4-Chloro-benzylsulfanyl)-5-(6-methoxy-pyridin-2-ylamino)-isothiazole-4-carboxylic acid amide | 407.0 | 2.1 | A |
| 34 (preparation #4) | 3-[1-(4-Chloro-phenyl)-propylsulfanyl]-5-(5-methyl-pyridin-2-ylamino)-isothiazole-4-carboxylic acid amide | 419.0 | 3.3 | A |
| 35 (preparation #4) | 3-[1-(4-Chloro-phenyl)-propylsulfanyl]-5-(6-methyl-pyridin-2-ylamino)-isothiazole-4-carboxylic acid amide | 419.0 | 3.4 | A |
| 36 (preparation #4) | 3-[1-(4-Chloro-phenyl)-propylsulfanyl]-5-(3-methyl-pyridin-2-ylamino)-isothiazole-4-carboxylic acid amide | 419.0 | 3.3 | A |
| 37 (preparation #4) | 3-[1-(4-Chloro-phenyl)-propylsulfanyl]-5-(2-isopropyl-pyridin-4-ylamino)-isothiazole-4-carboxylic acid amide | 445.9 | 1.8 | A |

TABLE I-continued

| Example No. (preparation #) | Name | LRMS (M+) | HPLC retention time (min) | HPLC Method |
|---|---|---|---|---|
| 38 (preparation #4) | 3-[1-(4-Chloro-phenyl)-propylsulfanyl]-5-(6-methyl-pyridin-3-ylamino)-isothiazole-4-carboxylic acid amide | 418 | 1.9 | A |
| 39 (preparation #4) | 3-[1-(4-Chloro-phenyl)-propylsulfanyl]-5-(pyrimidin-5-ylamino)-isothiazole-4-carboxylic acid amide | 405 | 2.5 | A |

What is claimed is:

1. A compound of the formula

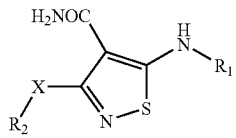

or a pharmaceutically acceptable salt, prodrug, solvate or hydrate thereof, wherein:

X is O or S;

$R^1$ is a 4–10 membered heterocyclic aromatic ring, optionally substituted with 1–4 $R^3$ groups, said $R^1$ group is optionally fused to a 4–10 membered aryl or heterocyclic group, said 4–10 membered aryl or heterocyclic groups are optionally substituted by 1 to 3 $R^3$ groups and 1 or 2 carbon atoms in the foregoing heterocyclic moiety are optionally substituted by an oxo (=O) moiety;

$R^2$ is H, $C_1$–$C_{10}$ alkyl, $C_3$–$C_{10}$ cycloalkyl, $C_2$–$C_{10}$ alkenyl, $C_2$–$C_{10}$ alkynyl, —$(CR^3R^3)_t(C_6$–$C_{10}$ aryl), or —$(CH_2)_t$ (5–10 membered heterocyclic), wherein t is an integer from 0 to 5; said alkyl group optionally includes 1 or 2 hetero moieties selected from O, S and —N($R^5$)— with the proviso that two O atoms, two S atoms, or an O and S atom are not attached directly to each other; said cycloalkyl, aryl and heterocyclic $R^2$ groups are optionally fused to a $C_6$–$C_{10}$ aryl group, a $C_5$–$C_8$ saturated cyclic group, or a 5–10 membered heterocyclic group; 1 or 2 carbon atoms in the foregoing heterocyclic moieties are optionally substituted by an oxo (=O) moiety; the —$(CH_2)_t$— moieties of the foregoing $R^2$ groups optionally include a carbon-carbon double or triple bond where t is an integer from 2 to 5, and the foregoing $R^2$ groups are optionally substituted by 1 to 5 $R^3$ groups;

each $R^3$ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^4$, —$C(O)R^4$, —$C(O)OR^4$, —$NR^5C(O)OR^4$, —$OC(O)R^4$, —$NR^5SO_2R^4$, —$SO_2NR^4R^5$, —$NR^5C(O)R^4$, —$C(O)NR^4R^5$, —$NR^4R^5$, —$S(O)_jR^4$ wherein j is an integer ranging from 0 to 2, —$SO_3H$, —$NR^4(CR^5R^6)_tOR^5$, —$(CH_2)_t(C_6$–$C_{10}$ aryl), —$SO_2(CH_2)_t(C_6$–$C_{10}$ aryl), —$S(CH_2)_t(C_6$–$C_{10}$ aryl), —$O(CH_2)_t(C_6$–$C_{10}$ aryl), —$(CH_2)_t$(5–10 membered heterocyclic), and —$(CR^5R^6)_mOR^5$, wherein m is an integer from 1 to 5 and t is an integer from 0 to 5; said alkyl group optionally contains 1 or 2 hetero moieties selected from O, S and —N($R^5$)— with the proviso that two O atoms, two S atoms, or an O and S atom are not attached directly to each other; said aryl and heterocyclic $R^3$ groups are optionally fused to a $C_6$–$C_{10}$ aryl group, a $C_5$–$C_8$ saturated cyclic group, or a 5–10 membered heterocyclic group; 1 or 2 carbon atoms in the foregoing heterocyclic moieties are optionally substituted by an oxo (=O) moiety; and the alkyl, aryl and heterocyclic moieties of the foregoing $R^3$ groups are optionally substituted by 1 to 3 substituents independently selected from halo, cyano, nitro, trifluoromethyl, trifluoromethoxy, azido, —$NR^5SO_2R^4$, —$SO_2NR^4R^5$, —$C(O)R^4$, —$C(O)OR^4$, —$OC(O)R^4$, —$NR^5C(O)R^4$, —$C(O)NR^4R^5$, —$NR^4R^5$, —$(CR^5R^6)_mOR^5$ wherein m is an integer from 1 to 5, —$OR^4$ and the substituents listed in the definition of $R^4$;

each $R^4$ is independently selected from H, $C_1$–$C_{10}$ alkyl, —$(CH_2)_t(C_6$–$C_{10}$ aryl), and —$(CH_2)_t$(5–10 membered heterocyclic), wherein t is an integer from 0 to 5; said alkyl group optionally includes 1 or 2 hetero moieties selected from O, S and —N($R^5$)— with the proviso that two O atoms, two S atoms, or an O and S atom are not attached directly to each other; said aryl and heterocyclic $R^4$ groups are optionally fused to a $C_6$–$C_{10}$ aryl group, a $C_5$–$C_8$ saturated cyclic group, or a 5–10 membered heterocyclic group; and the foregoing $R^4$ substituents, except H, are optionally substituted by 1 to 3 substituents independently selected from halo, cyano, nitro, trifluoromethyl, trifluoromethoxy, azido, —$C(O)R^5$, —$C(O)OR^5$, —$CO(O)R^5$, —$NR^5C(O)R^6$, —$C(O)NR^5R^6$, —$NR^5R^6$, hydroxy, $C_1$–$C_6$ alkyl, and $C_1$–$C_6$ alkoxy; and each $R^5$ and $R^6$ is independently H or $C_1$–$C_6$ alkyl.

2. The compound of claim 1, wherein $R^1$ is a 5–6 membered nitrogen containing aromatic heterocyclic ring.

3. The compound of claim 2, wherein the 5–6 membered nitrogen containing aromatic heterocyclic ring is selected from the group consisting of 3-pyrazolyl, 2-pyridyl, 3-pyridyl, 4-pyridyl, 2-pyrimidyl and 4-pyrimidyl.

4. The compound of claim 1, wherein is $R^2$ is $C_1$–$C_4$ alkyl, —$(CR^3R^3)_t(C_6$–$C_{10}$ aryl), or —$(CH_2)_t$(5–10 membered heterocyclic).

5. The compound of claim 4, wherein $C_1$–$C_4$ alkyl is methyl, ethyl or propyl.

6. The compound of claim 5, wherein the methyl, ethyl or propyl group is substituted by a cyclohexyl group.

7. The compound of claim 5, wherein said methyl, ethyl or propyl is substituted by a —$(CR^3R^3)_t(C_6$–$C_{10}$ aryl) group.

8. The compound of claim 4, wherein $R^2$ is —$(CR^3R^3)_t(C_6$–$C_{10}$ aryl).

9. The compound of claim 8, wherein $R^2$ is —$C(C_1$–$C_{10}$ alkyl)$_2(C_6$–$C_{10}$ aryl).

10. The compound of claim 9, wherein $R^2$ is —$C(H)(C_1$–$C_{10}$ alkyl)($C_6$–$C_{10}$ aryl).

11. The compound of claim 10, wherein R² is —C(H)(C₁–C₄ alkyl)(C₆–C₁₀ aryl).

12. The compound of claim 11, wherein R² is —C(H)(C₁–C₄ alkyl)(phenyl).

13. The compound of claim 12, wherein R² is —C(H)(methyl)(phenyl), —C(H)(ethyl)(phenyl), or —C(H)(propyl)(phenyl).

14. The compound of claim 13, wherein said phenyl moiety of R² is optionally substituted by 1 to 4 substituents independently selected from halo and C₁–C₄ alkyl.

15. The compound of claim 8, wherein said —(CR³R³)ₜ(C₆–C₁₀ aryl) group is benzyl optionally substituted by 1 to 4 substituents independently selected from halo and C₁–C₄ alkyl.

16. The compound of claim 1, wherein X is S and R² is —(CR³R³)ₜ(C₆–C₁₀ aryl).

17. The compound of claim 16, wherein R² is —C(H)(methyl)(phenyl), —C(H)(ethyl)(phenyl), or —C(H)(propyl)(phenyl).

18. A compound according to claim 1 selected from the group consisting of:
   3-Cyclohexylmethoxy-5-(pyrimidin-4-ylamino)-isothiazole-4-carboxylic acid amide
   3-Cyclohexylmethoxy-5-(pyrimidin-2-ylamino)-isothiazole-4-carboxylic acid amide
   3-cyclohexylmethoxy-5-(pyridin-2-ylamino)-isothiazole-4-carboxylic acid amide
   3-Cyclohexylmethoxy-5-(3-methyl-pyridin-2-ylamino)-isothiazole-4-carboxylic acid amide
   3-Cyclohexylmethoxy-5-(pyridin-3-ylamino)-isothiazole-4-carboxylic acid amide
   3-Cyclohexylmethoxy-5-(pyridin-4-ylamino)-isothiazole-4-carboxylic acid amide
   3-Cyclohexylmethoxy-5-(1H-pyrazol-3-ylamino)-isothiazole-4-carboxylic acid amide
   5-(1H-Benzoimadazol-2-ylamino)-3-cyclohexylmethoxy-isothiazole-4-carboxylic acid amide monoformate salt
   3-(4-Chloro-benzylsulfanyl)-5-(pyridin-3-ylamino)-isothiazole-4-carboxylic acid amide
   3-[1-(4-Chloro-phenyl)-propylsulfanyl]-5-(pyridin-3-ylamino)-isothiazole-4-carboxylic acid amide
   3-[1-(4-Chloro-phenyl)-ethylsulfanyl]-5-(pyridin-3-ylamino)-isothiazole-4-carboxylic acid amide
   3-(4-Chloro-benzylsulfanyl)-5-(pyridin-4-ylamino)-isothiazole-4-carboxylic acid amide
   3-(2-Chloro-benzylsulfanyl)-5-(pyridin-4-ylamino)-isothiazole-4-carboxylic acid amide
   3-(4-Chloro-benzylsulfanyl)-5-(6-methoxy-pyridin-3-ylamino)-isothiazole-4-carboxylic acid amide
   3-(4-Chloro-benzylsulfanyl)-5-(pyrimidin-4-ylamino)-isothiazole-4-carboxylic acid amide
   3-(4-Chloro-benzylsulfanyl)-5-(pyrazin-2-ylamino)-isothiazole-4-carboxylic acid amide
   3-(2-Chloro-benzylsulfanyl)-5-(pyridin-3-ylamino)-isothiazole-4-carboxylic acid amide
   3-(1-Phenyl-propylsulfanyl)-5-(pyridin-3-ylamino)-isothiazole-4-carboxylic acid amide
   3-(4-Chloro-benzylsulfanyl)-5-(pyridin-2-ylamino)-isothiazole-4-carboxylic acid amide
   3-(4-Chloro-benzylsulfanyl)-5-(pyrimidin-2-ylamino)-isothiazole-4-carboxylic acid amide
   3-(4-Chloro-benzylsulfanyl)-5-(6-methoxy-pyridin-2-ylamino)-isothiazole-4-carboxylic acid amide
   3-[1-(4-Chloro-phenyl)-propylsulfanyl]-5-(5-methyl-pyridin-2-ylamino)-isothiazole-4-carboxylic acid amide
   3-[1-(4-Chloro-phenyl)-propylsulfanyl]-5-(6-methyl-pyridin-2-ylamino)-isothiazole-4-carboxylic acid amide
   3-[1-(4-Chloro-phenyl)-propylsulfanyl]-5-(3-methyl-pyridin-2-ylamino)-isothiazole-4-carboxylic acid amide
   3-[1-(4-Chloro-phenyl)-propylsulfanyl]-5-(6-methyl-pyridin-3-ylamino)-isothiazole-4-carboxylic acid amide
   and the pharmaceutically acceptable salts, prodrugs and solvates of said compounds.

* * * * *